(12) United States Patent
Pizzo et al.

(10) Patent No.: US 8,076,059 B2
(45) Date of Patent: Dec. 13, 2011

(54) ADJUVANT CAPABLE OF SPECIFICALLY ACTIVATING THE ADAPTIVE IMMUNE RESPONSE

(75) Inventors: Salvatore V. Pizzo, Bahama, NC (US); Justin P. Hart, Durham, NC (US); James B. McLachlan, Raleigh, NC (US); Herman F. Staats, Hillsborough, NC (US); Soman N. Abraham, Chapel Hill, NC (US)

(73) Assignee: Duke University, Durham, NC (US)

( * ) Notice: Subject to any disclaimer, the term of this patent is extended or adjusted under 35 U.S.C. 154(b) by 612 days.

(21) Appl. No.: 10/817,023

(22) Filed: Apr. 2, 2004

(65) Prior Publication Data

US 2005/0031630 A1 Feb. 10, 2005

Related U.S. Application Data

(60) Provisional application No. 60/510,328, filed on Oct. 10, 2003, provisional application No. 60/463,300, filed on Apr. 16, 2003.

(51) Int. Cl.
*A61K 45/00* (2006.01)
(52) U.S. Cl. .......................................... 435/4; 424/278.1
(58) Field of Classification Search .................. None
See application file for complete search history.

(56) References Cited

U.S. PATENT DOCUMENTS

| | | | |
|---|---|---|---|
| 4,652,629 A | 3/1987 | Patrick et al. | |
| 4,834,976 A * | 5/1989 | Rosok et al. | 424/150.1 |
| 5,626,844 A | 5/1997 | Lemley et al. | |
| 6,270,758 B1 | 8/2001 | Staats et al. | |
| 6,271,202 B1 | 8/2001 | Kudsk | |
| 6,375,944 B1 * | 4/2002 | Trinchieri et al. | 424/85.2 |
| 6,413,935 B1 | 7/2002 | Sette et al. | |
| 7,105,171 B2 | 9/2006 | Stephens et al. | |
| 2002/0058293 A1 * | 5/2002 | Takesako et al. | 435/7.31 |
| 2005/0063978 A1 | 3/2005 | Fritz et al. | |

FOREIGN PATENT DOCUMENTS

WO WO02/32451 4/2002

OTHER PUBLICATIONS

Mielcarek et al. Interaction of *Bordetella pertussis* with mast cells, modulation of cytokine secretion by pertussis toxin. Cellular Microbiology, Mar. 2001, vol. 3, No. 3, 181-188.*
Lenney et al. Antimicrobial action of Compound 48/80 against protozoa, bacteria and fungi. Journal of Pharmaceutical Sciences. May 1997, vol. 66, No. 5, 702-705.*
Hood et al. Immunology, 2nd Edition. The Benjamin/Cummings Publishing Company, Inc., California, 1984, 371-373.*
Lenney et al. Antimicrobial Action of Compound 48/80 against protozoa, bacteria and fungi. Journal of Pharmaceutical Sciences, May 1977, vol. 66, No. 5, 702-705.*
Lenney et al. "Antimicrobial Action of Compound 48/80 against Protozoa, Bacteria and Fungi." *Journal of Pharmaceutical Sciences*, 1997. vol. 66, No. 5, pp. 702-705.
Malaviya et al. "Mast Cell modulation of neutrophil influx and bacterial clearance at sites of infection through TNF-alpha." *Nature*, 1996. vol. 381, pp. 77-80.
PCT International Search Report for International Application No. PCT/US04/10429, Mailed Aug. 12, 2005 (2 pages).
SIGMA. Compound 48/80, Sigma product No. C2313, Dec. 15, 1997, Saint Louis. (2 pages).
Fritz et al. (2004) "The Artificial Antimicrobial Peptide KLKLLLLLKLK Induces Predominantly a $T_H2$-type immune response to co-injected antigens." Vaccine 22, pp. 3274-3284.
Dorland's Illustrated Medical Dictionary, 25th Ed. (1974), pp. 764-765. W.B. Saunders, Philadelphia.
Specific Immunity: Active and passive immunity. University of Auckland Immunisation Advisory Centre (IMAC) NZ. (2008), 2 pp, printed Sep. 2, 2008.

* cited by examiner

*Primary Examiner* — Stacy B. Chen
(74) *Attorney, Agent, or Firm* — Myers Bigel Sibley & Sajovec, P.A.

(57) ABSTRACT

A composition for eliciting an immune response to an immunogen comprises an immunogen in combination with a mast cell membrane activator such as compound 48/80. Any suitable immunogen may be employed, such as an antibody-inducing determinant, a lipid, a peptide (e.g., an antibody-inducing peptide), a carbohydrate, an immunogen derived from a virus or cancer cell, etc. Methods of use are also described.

18 Claims, 11 Drawing Sheets

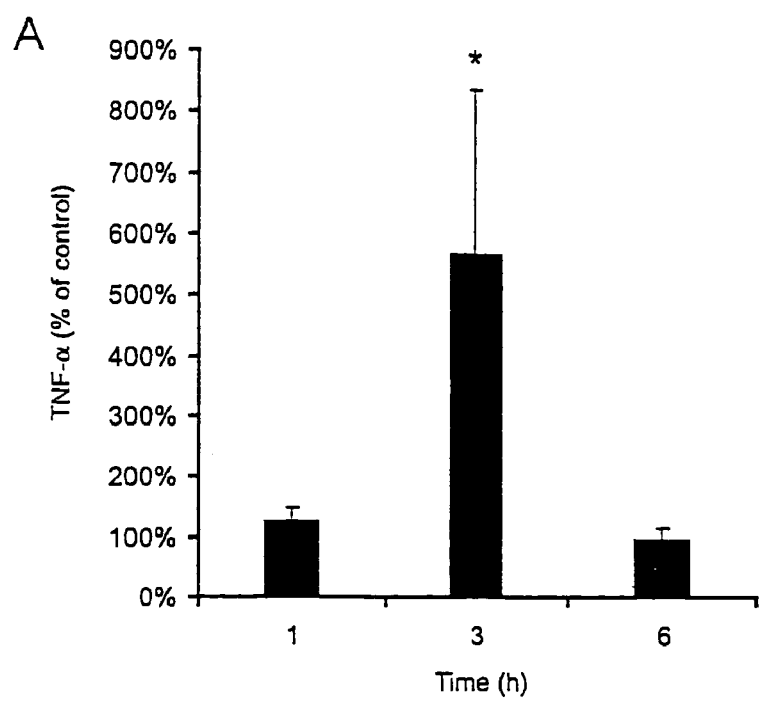
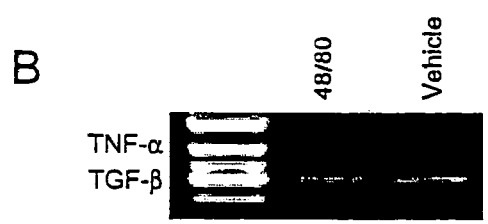
FIG 3

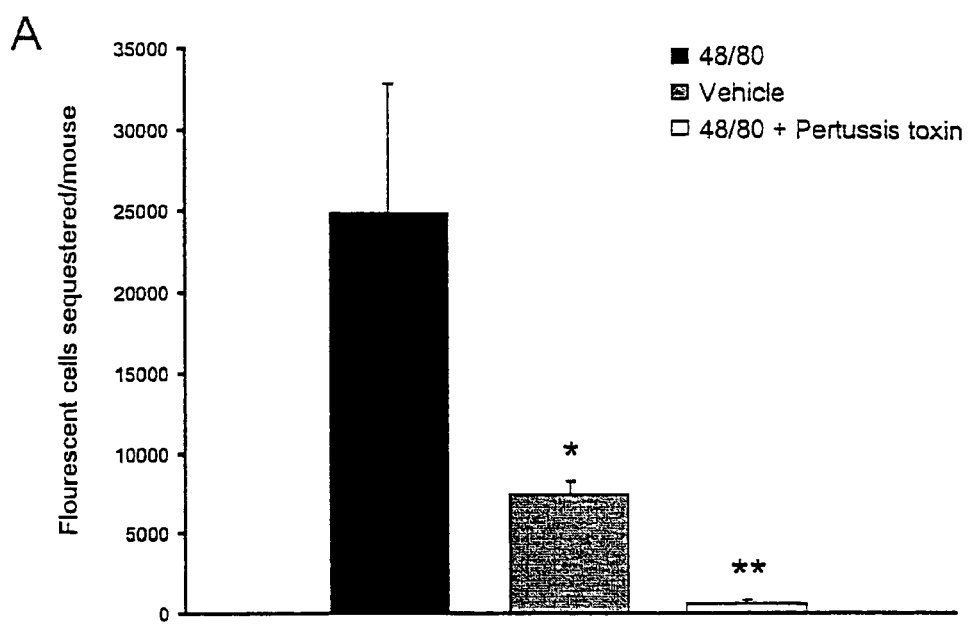
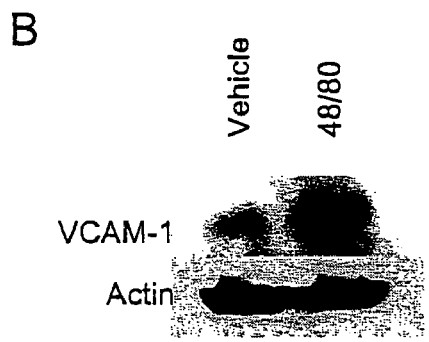
FIG 4

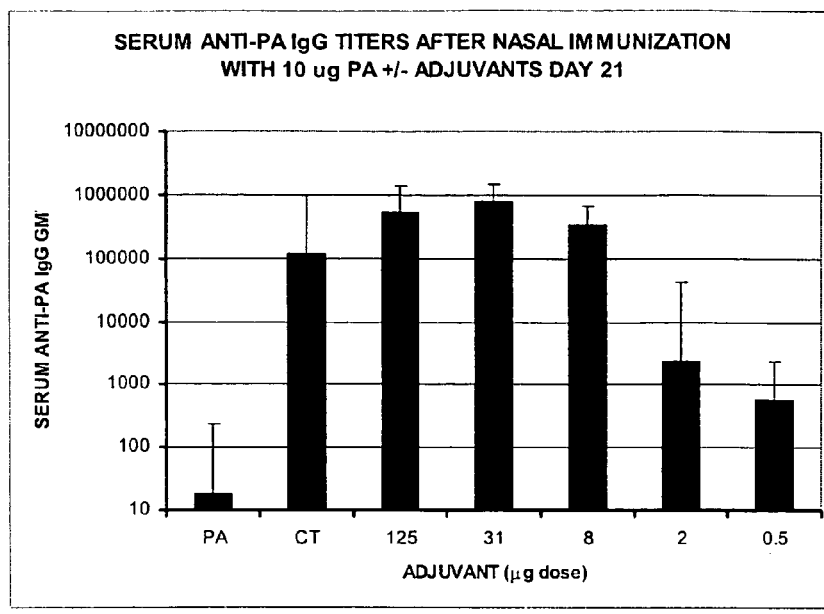
Fig 5A. P-values for adjuvant activity compared to PA alone: CT = 0.0000002; 48/80, 125μg = 0.000001; 48/80, 31μg = 0.0000006; 48/80, 8μg = 0.0000000007; 48/80, 2μg = 0.005; 48/80, 0.5μg = 0.02
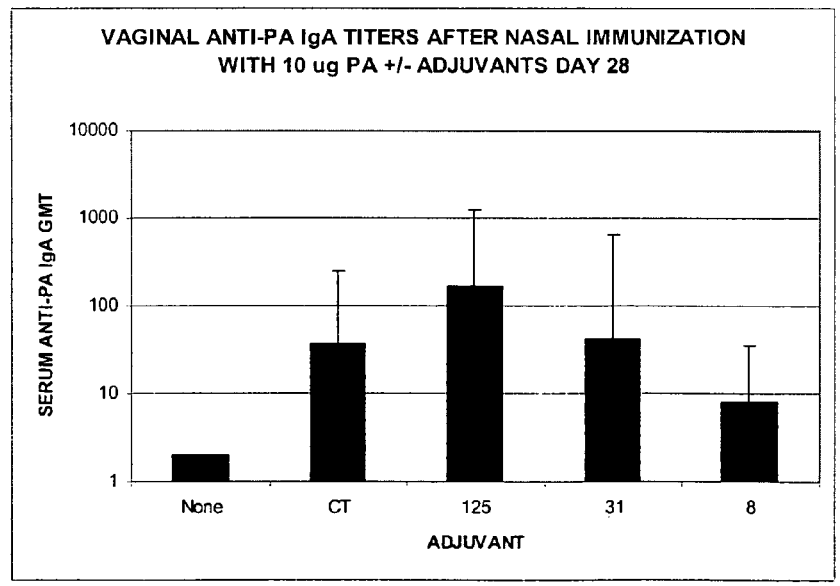
Fig 5B. P-values for adjuvant activity compared to PA alone: CT = 0.009; 48/80, 125μg = 0.001; 48/80, 31μg = 0.04; 48/80, 8μg = 0.07.

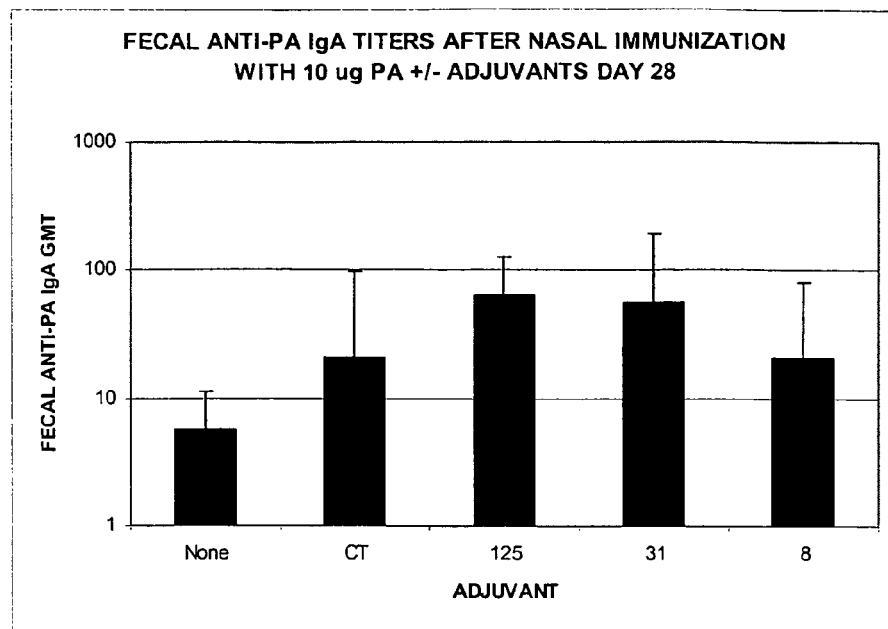
Fig 5C. P-values for adjuvant activity compared to PA alone: CT = 0.02; 48/80, 125µg = 0.001; 48/80, 31µg = 0.01; 48/80, 8µg = 0.12
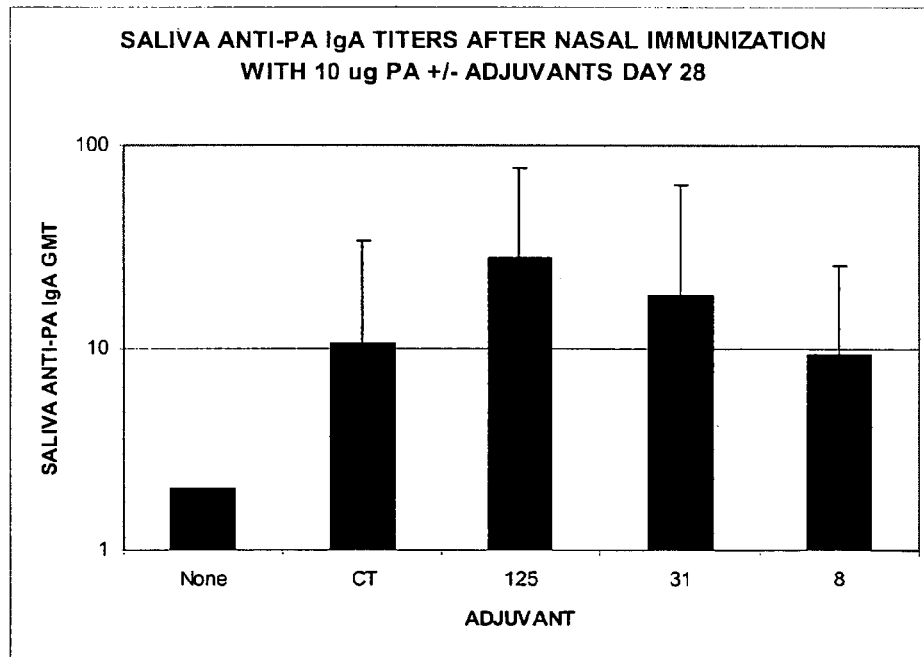
Fig 5D. P-values for adjuvant activity compared to PA alone: CT = 0.02; 48/80, 125µg = 0.001; 48/80, 31µg = 0.01; 48/80, 8µg = 0.02

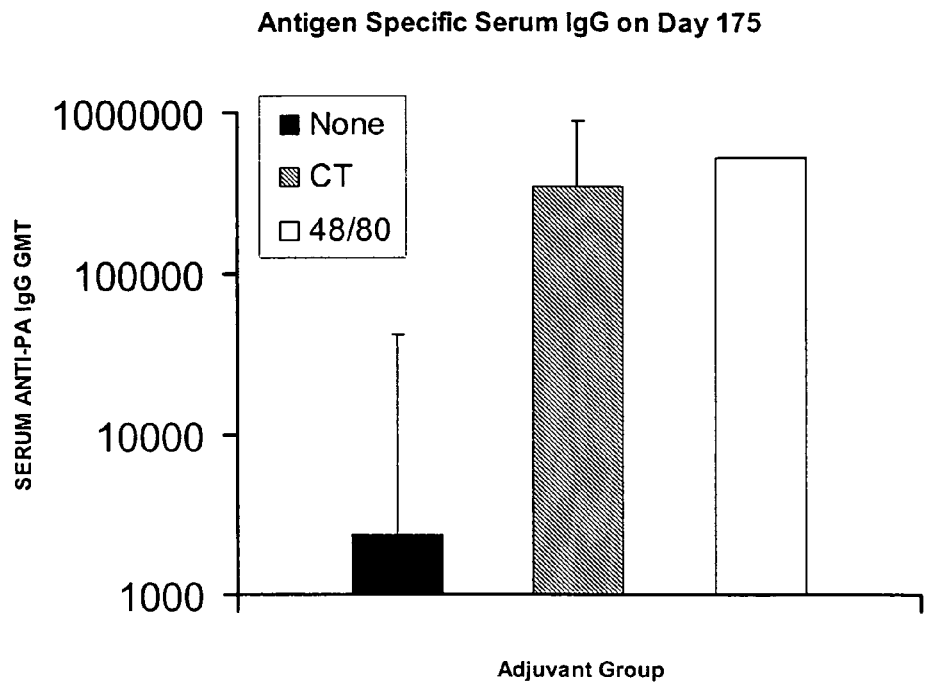
Fig 6. P-values for adjuvant activity compared to PA alone: CT = 0.006; 48/80, 8µg = 0.003.
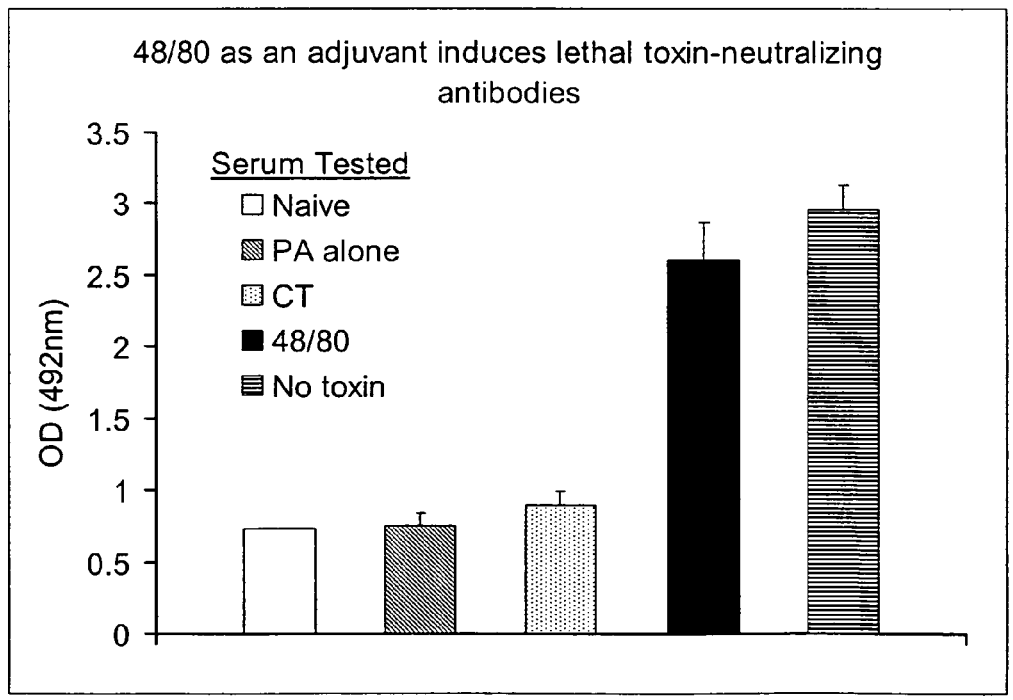
Figure 7

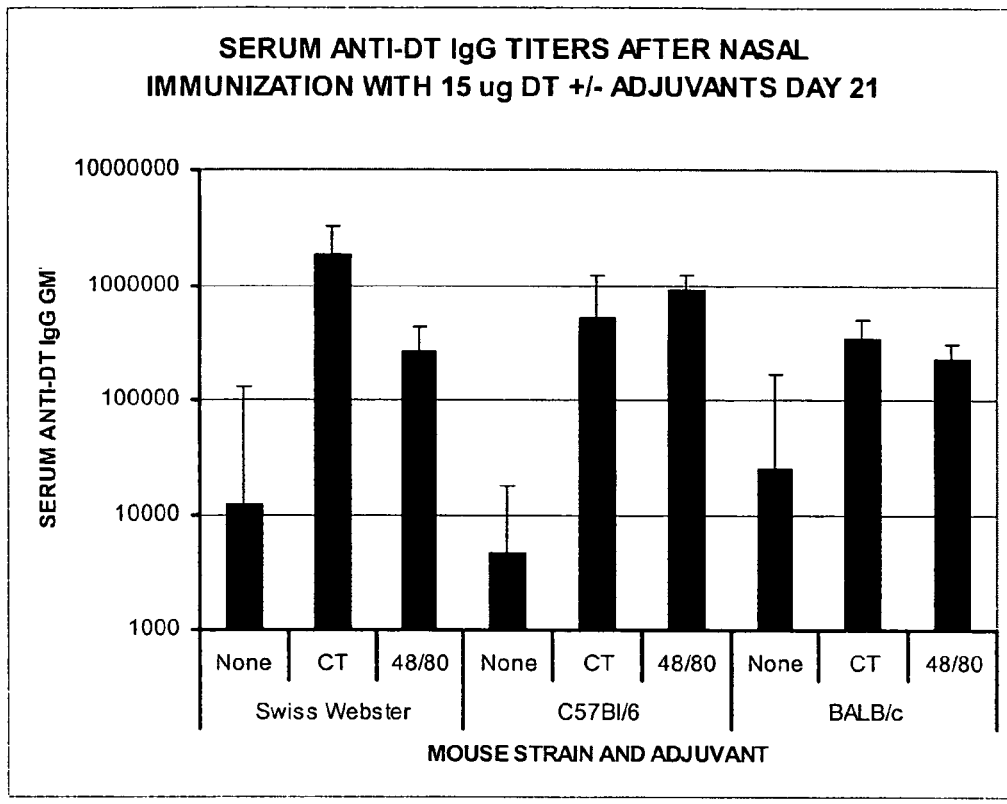
Fig. 8. P-values for adjuvant activity compared to DT alone: *Swiss Webster:* CT = 0.002; 48/80 = 0.02; *C57Bl/6;* CT = 0.0002; 48/80 = 0.00003; *BALB/c:* CT = 0.02; 48/80 = 0.03.

FIG. 9 Co-injection of Compound 48/80 with *Salmonella typhimurium* into the peritoneal cavities of mice markedly reduces bacterial growth.

As shown in the figure, mice have limited capability to control the in vivo growth of Salmonella. Notice the marked effect of compound 48/80 in reducing bacterial growth.

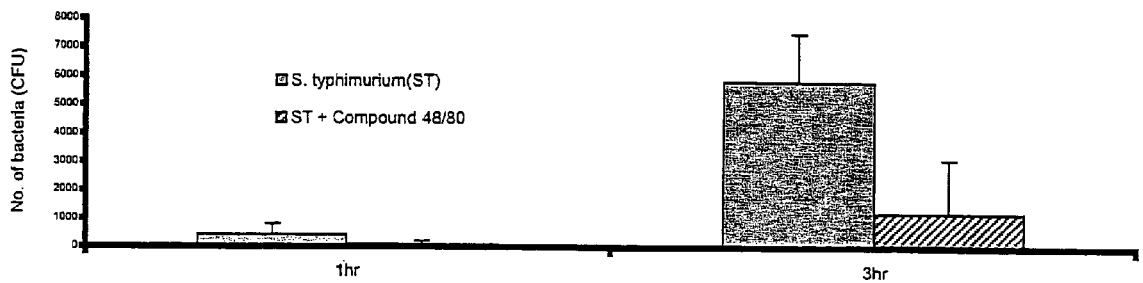

FIG. 10 Addition of Compound 48/80 at the site of bacterial instillation (peritoneum) markedly reduces the ability of Salmonella to migrate into and colonize other body sites.

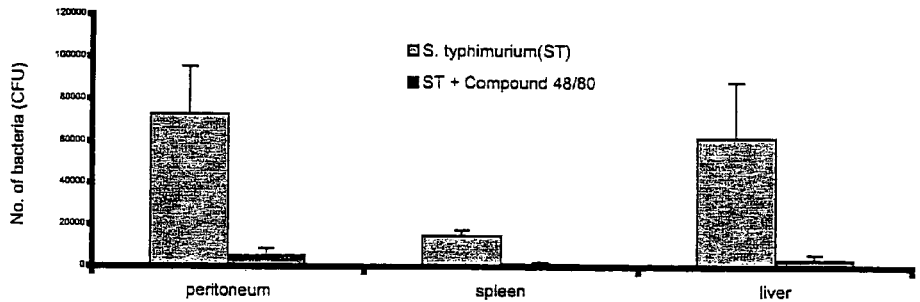

This figure shows effect of compound 48/80 on systemic spread of Salmonella to other more distal sites.

FIG 11 Addition of Compound 48/80 at sites of infection (peritoneal cavity) markedly increases local production of several neutrophil chemoattractants. Each of these chemoattractants is typically produced by activated mast cells.

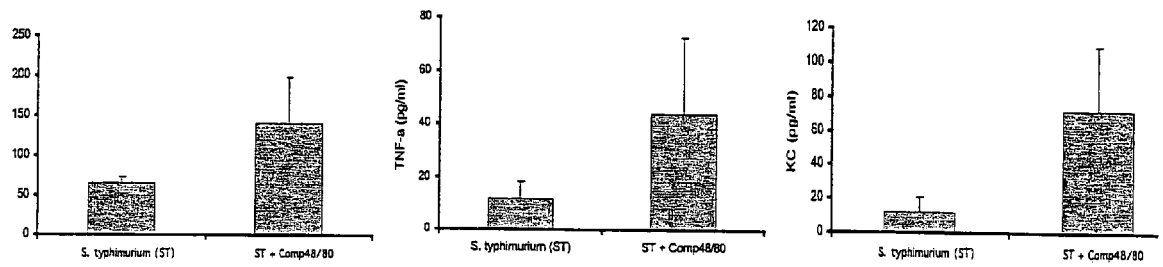

FIG 12 Instillation of compound 48/80 into the peritoneal cavities of mice results in increased recruitment of neutrophils compared to controls instilled only with *Salmonella*

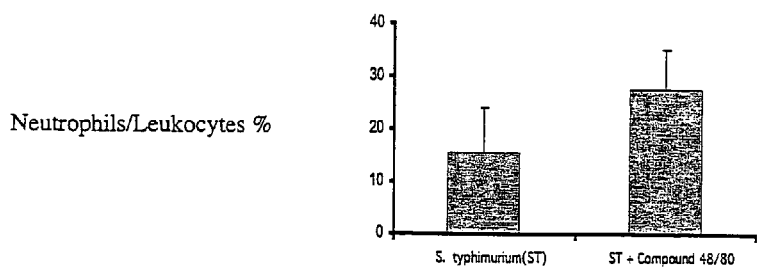

The increased levels of neutrophils in 48/80 treated mice correlates with increased presence of mast cell chemoattractants (Fig. 3). This data also correlates with increased bacterial clearance in 48/80 treated mice (Fig. 1). Note that neutrophils represent the major cell type responsible for clearance of Salmonella.

Protective effect of compound 48/80 when given orally to *Salmonella* infected mice. The agent was given 2 hrs after lethal dose of *Salmonella* was orally instilled.

US 8,076,059 B2

ADJUVANT CAPABLE OF SPECIFICALLY ACTIVATING THE ADAPTIVE IMMUNE RESPONSE

RELATED APPLICATIONS

This application claims the benefit of U.S. Provisional Patent Application Ser. No. 60/510,328, filed Oct. 10, 2003, and U.S. Provisional Patent Application Ser. No. 60/463,300, filed Apr. 16, 2003, the disclosures of which are incorporated by reference herein in their entirety.

This invention was made with Government support under grant no. R37-DK50814-23 from the National Institutes of Health. The Government has certain rights to this invention.

FIELD OF THE INVENTION

The present invention concerns methods and compositions useful for inducing an antigenic or immunogenic response in an animal subject.

BACKGROUND OF THE INVENTION

The development and application of vaccines for use in humans has had numerous shortcomings. To date, the adjuvants that have been best characterized include Freund's complete and incomplete adjuvant, and alum. Freund's and its variations have shown much promise in inducing immunostimulation and enhancing specific immune responses against protein antigens. However, it is presently not acceptable for use in humans due to unacceptable tissue damage and necrosis following its application (Aucouturier et al., *Vaccine* 19: 2666-2671 (2001)). Similar results have been found with incomplete Freund's, which lacks some pathogenic material. The alternative, alum, has a good safety record, but it is a weak adjuvant for the induction of antibodies against protein antigens (O'Hagan et al., *Biomolecular Engineering* 18: 69-85 (2001)). Moreover, alum adjuvants can induce IgE antibody response and have been associated with allergic responses in some subjects.

Located preferentially at the host's interface with the surrounding environment, mast cells have the capacity to rapidly release many presynthesized mediators e.g. TNF-α, histamine, and tryptase, which are stored within abundant, specialized intracellular granules (J. Marshall and J. Bienenstock, *Curr Opin Immunol* 6, 853-9 (December, 1994)). Because of their intrinsic capacity to undergo repeated cycles of degranulation and regranulation, mast cells are major mediators of inflammation in the host. Indeed, mast cells have been implicated in several pathophysiological conditions including, asthma, allergy, inflammatory bowel disease and arthritis (1). More recently, mast cells were reported to mediate the recruitment of neutrophils to sites of bacterial infection through this rapid release of TNF-α, which represents a critical physiological role for these cells and this cytokine in the innate immune response to infection (R. Malaviya et al., Abraham, *Nature* 381, 77-80 (May 2, 1996); B. Echtenacher et al., *Nature* 381, 75-7 (May 2, 1996)).

Draining nodes are dynamic lymphoid structures capable of entrapping large numbers of circulating lymphocytes in response to inflammatory stimuli. Within swollen nodes, newly recruited T cells interact with antigen loaded antigen presenting cells, a process which initiates the highly evolved adaptive immune system (M. K. Jenkins et al., *Annu Rev Immunol* 19, 23-45 (2001)). Currently, the exact mechanisms controlling lymph node hypertrophy in response to peripheral infection remain largely unknown.

SUMMARY OF THE INVENTION

A first aspect of the present invention is a composition for eliciting an immune response to an immunogen, the composition comprising, consisting of or consisting essentially of an immunogen in combination with a mast cell membrane activator such as compound 48/80. Any suitable immunogen may be employed, such as an antibody-inducing determinant, a lipid, a peptide (e.g., an antibody-inducing peptide), a carbohydrate, an immunogen derived from a virus or cancer cell, etc.

The composition described above may be provided in lyophilized form or in a pharmaceutically acceptable carrier such as a solid carrier or an aqueous carrier.

A second aspect of the present invention is a method of inducing an immune response comprising concurrently administering (e.g., simultaneously administering) an immunogen and a mast cell membrane activator such as compound 48/80 to a subject in an amount effective to produce an immune response therein. Administering may be carried out by any suitable procedure, such as parenteral, mucosal (e.g., intranasal, intragastric or oral, intrarrectal), or transcutaneous administration. The immune response may be a prophylactic immune response or a therapeutic immune response depending upon the purpose of the treatment, the immune response may comprise a humoral immune response and/or a cellular immune response.

A further aspect of the present invention is method of treating a microbial infection in a subject in need thereof, comprising administering a mast cell membrane activator such as compound 48/80 to said subject in an amount effective to treat the microbial infection.

A further aspect of the present invention is method of enhancing wound healing in a subject in need thereof, comprising administering (e.g., by topical administration to a wound or wound tissue) a mast cell membrane activator such as Compound 48/80 to a subject afflicted with a wound in an amount effective to enhance healing of the wound.

A method of reducing scar formation in a subject in need thereof, comprising administering (e.g., by topical administration to a wound or wound tissue) a mast cell membrane activator such as Compound 48/80 to a subject afflicted with a wound in an amount effective to reduce scar formation during healing of said wound.

A further aspect of the present invention is the use of a mast cell membrane activator such as compound 48/80 for the preparation of a medicament for carrying out a method as described herein.

The present invention is explained in greater detail in the drawings herein and the specification set forth below.

BRIEF DESCRIPTION OF THE DRAWINGS

FIG. 1A, Popliteal lymph node weights following injection of heat killed *E. coli* in the footpad (n=5-10 mice/timepoint) Asterisk, P=0.001 when compared with 0 time point; two asterisks, P<0.0001 when compared with 0 time point three asterisks, P=0.0001 when compared with 0 time point FIG. 1B, cross sections through the center of popliteal lymph nodes at 0 hours (top panel) and 24 hours (bottom panel) post-infection with heat-killed *E. coli*. Bar=10 μm—

FIG. 1C, Quantification of local mast cell numbers in footpads following infection. Mast cell numbers were determined by counting a minimum of 10 whole sections and quantified as the number of mast cells/section (n=4 footpads, >10 sections/footpad). By this method totally degranulated mast cells would not be detected. Asterisk, P=0.005 when compared with control; two asterisks, P=0.02 when compared with control—

FIG. 1D, Depiction of an average section from vehicle injected (top panel) and *E. coli* infected (bottom panel) footpads 4 hours following injection. Bar=10 μm. Mast cells stain dark purple against blue counterstaining. Inset depicts higher magnification of a mast cell from each section as indicated by the box. The mast cell in the lower inset represents a partially degranulated mast cell. Bar=1 μm—

FIG. 1E, Differences in popliteal lymph node weights between wild-type, mast cell deficient mice and mast cell deficient mice reconstituted with bone marrow mast cells after infection with *E. coli*. Data are depicted as a percentage of vehicle injected controls (n=3-6 mice) Asterisk, P=0.01 when compared with W/Wv; two asterisks, P=0.008 when compared with W/Wv—

FIG. 1F, Popliteal lymph node weights at 6 and 24 hours following injection of compound 48/80 in footpads of normal mice. Data are depicted as a percentage of vehicle injected controls (n=3 mice/timepoint) Asterisk, P=0.008 when compared with control. Bars represent the mean±s.d.

FIG. 2A, Popliteal lymph node weights in 48/80 activated mice following treatment with TNF-α specific antibody or an isotype control. Data are depicted as a percentage of vehicle injected controls (n=3 mice) Asterisk, P=0.03 when compared with control.

FIG. 2B, Popliteal lymph node weights in TNF-α deficient mice and wild type mice. Data are depicted as a percentage of vehicle injected controls 24 hours after injection of compound 48/80 (n=4-5 mice) Asterisk P=0.05 when compared with wild type mice.

FIG. 2C, Popliteal lymph node weights at 24 and 48 hours following direct instillation of 50 ng recombinant mouse TNF-α into the footpads of wild type mice. Data are depicted as a percentage of vehicle injected controls (n=3 mice) Asterisk, P=0.05 when compared with control; two asterisks, P=0.02 when compared with control.

FIG. 3 Increase in TNF-α in draining lymph nodes following peripheral mast cell activation.

FIG. 3A, ELISA of TNF-α protein in the popliteal lymph nodes of normal mice at 1, 3, and 6 hours after footpad injection with compound 48/80. Values are given as a percent of TNF-α in the lymph nodes of vehicle injected controls Asterisk, P=0.02 when compared with control (FIG. 3B)

FIG. 3B, Expression of TNF-α mRNA in popliteal lymph nodes of mice injected with compound 48/80 at 3 hours post-instillation as compared with vehicle injected controls. Constitutively expressed TGF-β is shown as a control message. Bars represent the mean±s.d.

FIG. 4 Mast cell mediated lymph node hypertrophy involves increased sequestration of T-cells and increased expression of VCAM-1 in lymph nodes—

FIG. 4A, Total number of CFSE labeled $CD4^+$ T-cells in pooled popliteal lymph nodes from each mouse (n=3-4 mice). Pertussis toxin or untreated T-cells were both labeled and injected intravenously immediately prior to compound 48/80 instillation into the footpads. Lymph nodes were removed 24 hours later and assayed for fluorescent cells by FACS. Control footpads were injected with vehicle alone. Asterisk, P=0.01 when compared with 48/80 alone; two asterisks, P=0.003 when compared with 48/80 alone—

FIG. 4B, Up-regulated expression of VCAM-1 in draining popliteal lymph nodes of mice treated with compound 48/80. Actin is shown as a protein loading control. Bars represent the mean±s.d.

FIG. 5 shows antigen-specific antibody (IgG and IgA) responses using compound 48/80 as an nasal vaccine adjuvant.

FIG. 5A shows mice nasally immunized with recombinant *Bacillus anthracis* protective antigen (rPA) alone or in the presence of cholera toxin (CT) or four-fold serial dilutions of compound 48/80 (48/80). Immunizations were instituted on days 0, 7, and 14. On day 21-22 (FIG. 5A), serum was collected and tested for the presence of anti-PA IgG. Both CT and 48/80 provided significant adjuvant activity at all doses tested as indicated by the anti-PA IgG geometric mean titers indicated on the graph at day 21-22 Compound 48/80 used at 125, 31 and 8 μg was as effective as CT when used as a nasal vaccine adjuvant based on antigen-specific IgG titers tested on day 21-22.

FIG. 5B-D shows mice nasally immunized with recombinant *Bacillus anthracis* protective antigen (rPA) alone or in the presence of cholera toxin (CT) two-fold serial dilutions of compound 48/80 (48/80). Immunizations were instituted on days 0, 7, and 14. On day 28 vaginal lavage, saliva and feces was collected and tested for the presence of anti-PA IgA. 48/80 provided significant adjuvant activity for the induction of vaginal and fecal antigen-specific IgA when used at 125 and 31 μg (FIGS. 5B and C respectively). 48/80 provided significant adjuvant activity for the induction of salivary antigen-specific IgA when used at 125, 31, and 8 μg (FIG. 5D).

FIG. 6 shows mice nasally immunized with 10 μg recombinant *Bacillus anthracis* protective antigen (rPA) alone or in the presence of cholera toxin (CT) or 8 μg compound 48/80 (48/80) on days 0, 7 and 14, On day 175, serum was collected and tested for the presence of anti-PA IgG by ELISA. Both CT and 48/80 showed a significant adjuvant activity over PA alone. This demonstrates the long lasting nature of 48/80 as an effective adjuvant.

FIG. 7 shows mice nasally immunized with recombinant *Bacillus anthracis* protective antigen (rPA) alone or in the presence of cholera toxin (CT) or in the presence of 125 μg compound 48/80 (48/80) produce functionally protective antibodies. Serum from immunized mice was incubated with rPA for 1 hour. Lethal factor from *Bacillus anthracis* was added forming lethal toxin which is capable of killing macrophages in cell culture. Cell viability was assessed after 4 hours and it was determined that 48/80 was capable of inducing protective antibodies in immunized mice even when serum was diluted to 1:32.

FIG. 8. Swiss Webster, C57B1/6, and BALB/c mice were nasally immunized with diphtheria toxoid (DT) plus or minus 48/80 to confirm the adjuvant activity of 48/80 when administered with a different antigen in various mouse strains. Mice were nasally immunized with 15 μg DT alone, with CT (1 μg, positive control) or 31 μg of 48/80. FIG. 8 shows that anti DT serum IgG responses in mice nasally immunized with 48/80 were significantly greater than anti DT serum IgG responses in mice nasally immunized with DT alone in all three mouse strains. These results indicate that 48/80 is an effective adjuvant in Swiss Webster, C57B1/6, and BALB/c mice.

FIG. 9 shows that co-injection of Compound 48/80 with *Salmonella typimurim* into the peritoneal cavities of mice markedly reduces bacterial growth.

FIG. 10 shows that the addition of Compound 48/80 at the site of bacterial instillation markedly reduces the ability of Salmonella to migrate into and colonize other body sites.

FIG. 11 shows that the addition of compound 48/80 at sites of infection markedly increases local production of several neutrophil chemoattractants.

FIG. 12 shows that instillation of compound 48/80 into the peritoneal cavities of mice results in increased recruitment of neutrophils compared to controls instilled only with Salmonella.

DETAILED DESCRIPTION OF THE PREFERRED EMBODIMENTS

Figure 1:
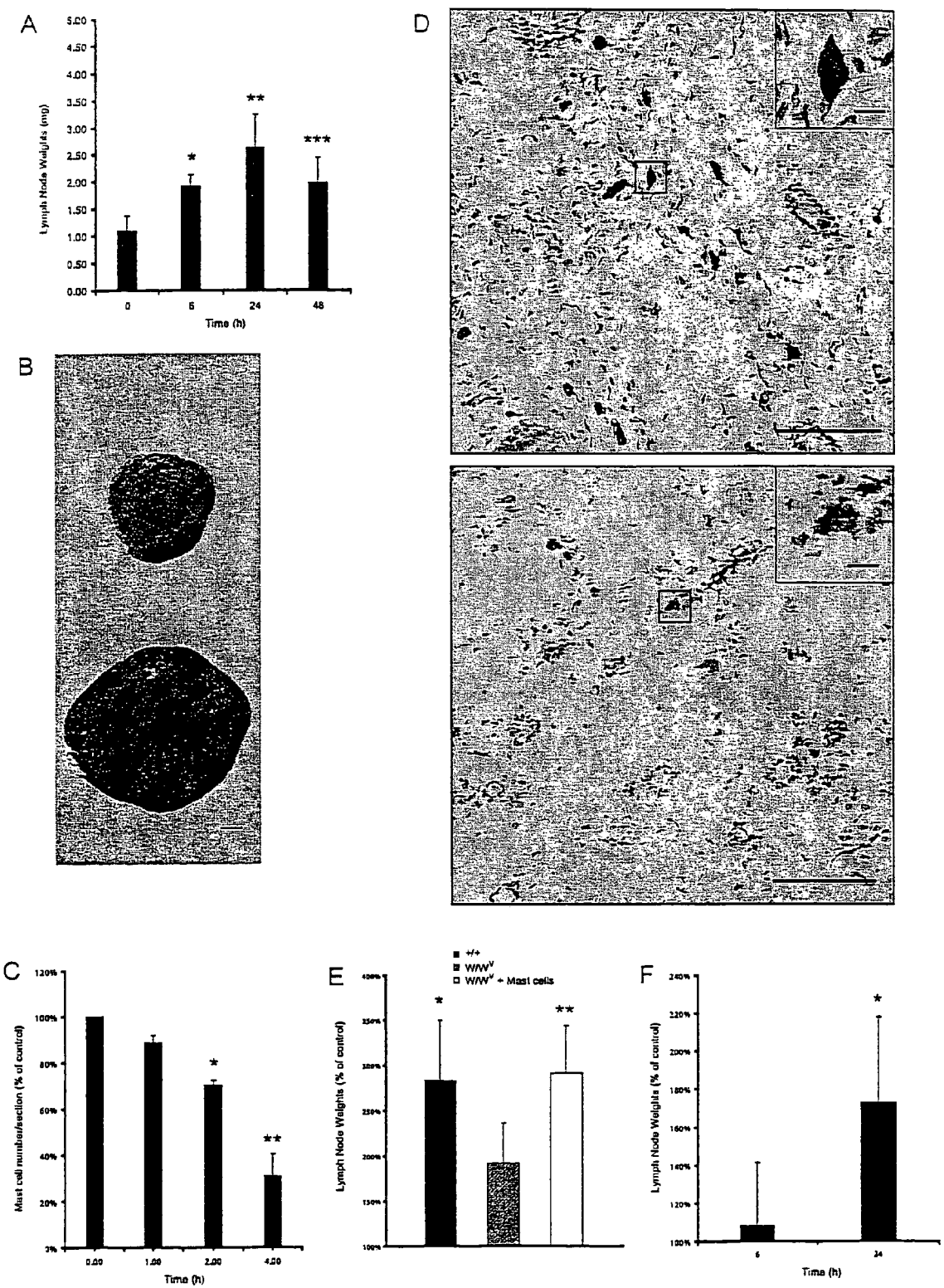
FIG. 1 Mast cell regulation of lymph node hypertrophy during infection.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All U.S. Patents cited herein are to be incorporated by reference herein in their entirety.

1. Definitions.

Subjects to be treated by the methods and compositions include both human subjects and animal subjects such as dogs, cats, rabbits, goats, horses, pigs, cattle, birds (e.g., chickens, turkeys, ducks, geese, quail, pheasant), etc (including both male and female subjects and subjects of all ages including infant, juvenile, adolescent and adult subjects; and for birds subjects in ovo). Subjects may be treated for any purpose, such as for of eliciting a protective immune response; for eliciting the production of antibodies in that subject (typically an animal subject) which antibodies then may be collected and used for other purposes such as diagnostic purposes or administering to other subjects to produce passive immunity therein, etc.

"Immunogen" and "antigen" are used interchangeably and mean any compound to which a cellular or humoral immune response is to be directed against. Non-living immunogens (e.g., killed immunogens, subunit vaccines, recombinant proteins or peptides or the like) are currently preferred.

As used herein, the term "antigenic determinant" is any structure that can elicit, facilitate, or be induced to produce an immune response, for example carbohydrate epitopes, lipids, proteins, peptides, or combinations thereof.

As used herein the term "infection" includes the presence of a microbe in or on a subject which, if its growth were inhibited, would result in a benefit to the subject. As such, the term "infection" in addition to referring to the presence of pathogens also includes normal flora which is not desirable, e.g., on the skin of a burn patient or in the gastrointestinal tract of an immunocompromised patient.

An oligopeptide or peptide as used herein refers to a chain of at least four amino acid or amino acid mimetics, preferably at least six, more preferably eight to ten, sometimes eleven to fourteen residues, and usually fewer than about fifty residues, more usually fewer than about twenty-five, and preferably fewer than fifteen, e.g., eight to fourteen residues. The oligopeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

"Concurrently administered" as used herein means that two compounds are administered sufficiently close in time to achieve a combined immunological effect. Concurrent administration may thus be carried out by sequential administration or simultaneous administration (e.g., simultaneous administration in a common, or the same, carrier).

1. Mast Cell Membrane Activators.

Compound 48/80 is know and available from commercial sources such as Sigma-Aldrich Co. as Product Number C2313. Compound 48/80 is an oligomeric mixture of condensation products of N-methyl-p-methoxyphenethylamine and formaldehyde. Compound 48/80 has been prepared and administered to humans and can be prepared for administration to human subjects in accordance with known techniques (Brunet et al., *Journal of Allergy & Clinical Immunology* 82; 398-402 (1988); Bedard et al., *Journal of Allergy & Clinical Immunology* 78: 1121-1125 (1986); Charpin et al., *Journal of Allergy & Clinical Immunology* 71: 363-370 (1983).

In general, compound 48/80 is believed to have the structure:

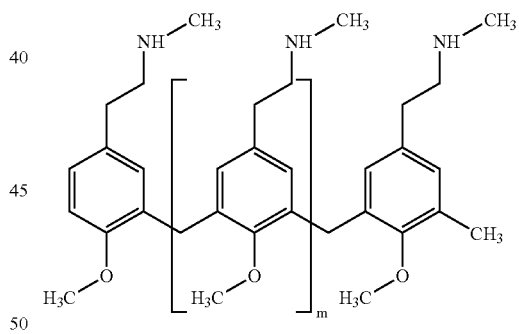

where m is 1 to 4. Thus compound 48/80 may be administered as a single oligomer (for example, preferably where m is 4), or may be administered as a mixture of oligomers of various chain lengths where m is between 1 and 4.

In addition to compound 48/80, those skilled in the art will appreciate that other compounds that are mast cell membrane activators may also be used to carry out the present invention. In general, any compound that induces a mast cell to secrete, or induces mast cell exocytosis, can be used. Examples of other suitable mast cell membrane activators in addition to compound 48/80 include, but are not limited to, polymixin B, mastoparan [M. Aridor et al., J Cell Biol, 111(3): 909-17 (1990), M. Aridor et al., Science, 262(5139): 1569-72 (1993)], substance P [M. Aridor et al., supra; T. Theoharides et al., Br J Pharmacol, 131(6): 1039-49 (2000)], neomycin [M. Aridor, supra, M. Aridor and R. Sagi-Eisenberg, J Cell Biol, 111(6 Pt 2): 2885-91 (1990)], analogs of compound 48/80, and additional molecules capable of binding IgE molecules bound on the mast cell membranes such as IgE-specific antibody or antigen [S. Mayr et al., J. Immunol. 169(4): 2061-8 (2002)].

Polycations can be utilized as mast cell membrane activators to carry out the present invention. Examples of suitable polycations include, but are not limited, polyethylenimines (particularly polyethylenimines with a molecular weight of 200 or 300 up to 2,000, such as polyethylenimine PEI6 (polyethylenimine with a molecular weight of 600)), polyallylamines, spermine, etc. See, e.g., T. Suzuki-Nishimura et al., *Gen. Pharmacol.* 26, 1171-8 (1995); T. Suzuki-Nishimura et al., *Japanes Journal of Pharmacol* 51, 279-290 (1989); H. Vliagoftis et al., *International Journal of Immunopharmacology* 21, 547-59 (1999).

2. Immunogens

The particular immunogen used (e.g., proteins, peptides, polysaccharides, lipids, and the like, including glycoproteins, glycolipids, glycoproteins, lipoproteins, lipopolysaccharides and the like) is not critical to the invention. For a listing of some suitable immunogens for use in the present invention, see, e.g., BioCarb Chemicals Catalogue; and The Jordan Report: Accelerated Development of Vaccine 1995 NIH, Bethesda, Md., 1995).

Examples of suitable immunogens include those derived from bacterial surface polysaccharides which can be used in carbohydrate-based vaccines. Bacteria typically express carbohydrates on their cell surface as part of glycoproteins, glycolipids, O-specific side chains of lipopolysaccharides, capsular polysaccharides and the like. Exemplary bacterial strains include *Streptococcus pneumonia, Neisseria meningitidis, Haemophilus influenza, Klebsiella* spp., *Pseudomonas* spp., *Salmonella* spp., *Shigella* spp., and Group B streptococci.

A number of suitable bacterial carbohydrate epitopes which may be used as the immunogen in the present invention are described in the art (e.g., Sanders, et al. Pediatr. Res. 37:812-819 (1995); Bartoloni, et al. Vaccine 13:463-470 (1995); Pirofski, et al., Infect. Immun. 63:2906-2911 (1995) and International Publication No. WO 93/21948) and are further described in U.S. Pat. No. 6,413,935.

Exemplary viral antigen- or immunogen includes those derived from HIV (e.g., gp120, nef, tat, pol). Exemplary fungal antigens include those derived from *Candida albicans, Cryptococcus neoformans, Coccidoides* spp., *Histoplasma* spp., and *Aspergillus* spp. Parasitic antigens include those derived from *Plasmodium* spp., *Trypanosoma* spp., *Schistosoma* spp., *Leishmania* spp. and the like.

Exemplary carbohydrate epitopes that may be utilized as antigens or immunogens in the present invention include bur are not limited to the following:

Gal$\alpha$1,4Gal$\beta$-(for bacterial vaccines); GalNAc$\alpha$-(for cancer vaccines);

Man$\beta$1,2(Man$\beta$)$_n$Man$\beta$-(for fungal vaccines useful against, for example, *Candida albicans*), where n=O→∞;

GalNAc$\beta$1,4(NeuAc$\alpha$2,3)Gal$\beta$1,4Glc$\beta$-O-ceramide. (for cancer vaccines);

Gal$\alpha$1,2(Tyv$\alpha$1,3)Man$\alpha$1,4Rha$\alpha$1,3Gal$\alpha$1,2(Ty$\alpha$1,3)Man$\alpha$4Rha- and Gal$\alpha$1,2(Abe$\alpha$1,3)Man$\alpha$1,4Rha$\alpha$1,3 Gal$\alpha$1,2(Abe$\alpha$1,3)Man$\alpha$1,4Rha$\alpha$1,3Gal$\alpha$1, 2 (Abe$\alpha$1,3)Man$\alpha$1,4Rha-(both of which are useful against, for example, *Salmonella* spp.)

Carbohydrate epitopes as antigens or immunogens and the synthesis thereof are described further in U.S. Pat. No. 6,413,935.

In one embodiment the immunogen may be an anthrax immunogen; i.e. an immunogen that produces protective immunity to *Bacillus anthracis*, such as anthrax vaccine, A, (Michigan Department of Health, Lansing, Mich.; described in U.S. Pat. No. 5,728,385). Other examples of immunogens or antigens include but are not limited to those that produce an immune response or antigenic response to the following diseases and disease-causing agents: adenoviruses; *Bordetella pertussus*; Botulism; bovine rhinotracheitis; *Branhamella catarrhalis*; canine hepatitis; canine distemper; Chlamydiae; Cholera; coccidiomycosis; cowpox; cytomegalovirus; cytomegalovirus; Dengue fever; dengue toxoplasmosis; Diphtheria; encephalitis; Enterotoxigenic *Escherichia coli*; Epstein Barr virus; equine encephalitis; equine infectious anemia; equine influenza; equine pneumonia; equine rhinovirus; feline leukemia; flavivirus; Globulin; *haemophilus influenza* type b; *Haemophilus influenzae; Haemophilus pertussis; Helicobacter pylori; Hemophilus*; hepatitis; hepatitis A; hepatitis B; Hepatitis C; herpes viruses; HIV; HIV-1 viruses; HIV-2 viruses; HTLV; Influenza; Japanese encephalitis; Klebsiellae species; *Legionella pneumophila; leishmania*; leprosy; lyme disease; malaria immunogen; measles; meningitis; meningococcal; Meningococcal Polysaccharide Group A, Meningococcal Polysaccharide Group C; mumps; Mumps Virus; mycobacteria and; *Mycobacterium tuberculosis; Neisseria; Neisseria gonorrhoeae; Neisseria meningitidis*; ovine blue tongue; ovine encephalitis; papilloma; parainfluenza; paramyxovirus; paramyxoviruses; Pertussis; Plague; *Pneumococcus; Pneumocystis carinii*; Pneumonia; *Poliovirus; Proteus* species; *Pseudomonas aeruginosa*; rabies; respiratory syncytial virus; *rotavirus*; Rubella; Salmonellae; schistosomiasis; Shigellae; simian immunodeficiency virus; Smallpox; *Staphylococcus aureus; Staphylococcus* species; *Streptococcus pneumoniae; Streptococcus pyogenes; Streptococcus* species; swine influenza; tetanus; *Treponema pallidum*; Typhoid; Vaccinia; varicella-zoster virus; and *Vibrio cholerae*. The antigens or immunogens may, include various toxoids, viral antigens and/or bacterial antigens such as antigens antigens commonly employed in the following vaccines: chickenpox vaccine; diphtheria, tetanus, and pertussis vaccines; *haemophilus influenzae* type b vaccine (Hib); hepatitis A vaccine; hepatitis B vaccine; influenza vaccine; measles, mumps, and rubella vaccines (MMR); pneumococcal vaccine; polio vaccines; *rotavirus* vaccine; anthrax vaccines; and tetanus and diphtheria vaccine (Td). See, e.g., U.S. Pat. No. 6,309,633.

Antigens or immunogens that are used to carry out the present invention include those that are derivatized or modified in some way, such as by conjugating or coupling one or more additional groups thereto to enhance function or achieve additional functions such as targeting or enhanced delivery thereof, including but not limited to those techniques described in U.S. Pat. No. 6,493,402 to Pizzo et al. ($\alpha$-2 macroglobulin complexes); U.S. Pat. No. 6,309,633; U.S. Pat. No. 6,207,157; U.S. Pat. No. 5,908,629, etc.

3. Pharmaceutical Compositions and Methods.

The compounds of the present invention, and pharmaceutical and vaccine compositions thereof, can be administered to subjects as described above for prophylactic and/or therapeutic purposes. The present invention can be used to elicit and/or enhance immune responses against immunogens. Examples of diseases or disorders which can be treated using the present invention are described above.

In therapeutic applications, the present invention is administered to an individual already suffering from the disorder of interest. Those in the incubation phase or the acute phase of the disease may be treated with the present invention separately or in conjunction with other treatments, as appropriate.

In therapeutic applications, a composition of the present invention is administered to a patient in an amount sufficient to elicit an effective immune response (e.g., a cellular immune response and/or a humoral immune response) response to the antigen and to treat, or at least partially arrest, symptoms and/or complications. An amount adequate to accomplish this is defined as "therapeutically effective dose." Amounts effective for this use will depend in part on the antigen composition, the manner of administration, the stage and severity of the disease being treated, the weight and general state of health of the patient, and the judgment of the prescribing physician.

Effective amounts of the compositions of the present invention, for the initial immunization that is for therapeutic or prophylactic administration, generally range from about 1 µg to about 10,000 µg of immunogen for a 70 kg patient, usually from about 100 to about 8000 µg, and preferably between about 200 and about 6000 µg. These doses may be followed by boosting dosages of from about 1.0 µg to about 1000 µg of immunogen pursuant to a boosting regimen over weeks to months depending upon the patient's response and condition by measuring specific immune responses.

The dosage of compound 48/80 or other mast cell membrane activator will vary depending upon the condition of the subject, the nature of the antigen or immunogen, the purity of the compound 48/80 (that is, delivered as a mixture of oligomers, or a composition consisting essentially of one particular monomer) or other mast cell membrane activator, but should in general be sufficient to enhance the efficacy of the antigen or immunogen in evoking an antigenic or immunogenic response (e.g., protective immunity). For example, the amount of compound 48/80 or other mast cell membrane activator administered may range from about 0.05, 0.1, 0.5 or 1 milligram per kilogram subject body weight, up to about 10, 50 or 100 milligrams per kilogram subject body weight, or more.

It must be kept in mind that the compositions of the present invention may generally be employed in serious disease states, that is, life-threatening or potentially life threatening situations. In such cases, in view of the minimization of extraneous substances and the relative nontoxic nature of the conjugates, it is possible and may be felt desirable by the treating physician to administer substantial excesses of these compositions.

Further, the present invention can be used prophylactically to prevent, treat, reduce, and/or ameliorate bacterial infections, viral infections, fungal infections, parasitic infections and cancer. Effective amounts are as described above. Additionally, one of ordinary skill in the vaccine arts would also know how to adjust or modify prophylactic treatments, as appropriate, for example by boosting and adjusting dosages and dosing regimes.

Therapeutic administration may begin at the first sign of disease or the detection or surgical removal of tumors or shortly after diagnosis in the case of acute infection. This is followed by boosting doses until symptoms are substantially abated and for a period thereafter. In chronic infection, initial high doses followed by boosting doses may be required.

Treatment of an infected individual with the compositions of the invention may hasten resolution of the infection in acutely infected individuals. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The present invention can also be used for the treatment of chronic infection and to stimulate the immune system to eliminate virus-infected cells in individuals with latent infections. It is important to provide an amount of compositions of the present invention in a formulation and mode of administration sufficient to effectively elicit and/or enhance an immune response. Thus, for treatment of chronic infection, a representative dose is in the range of about 1.0 µg to about 5000 µg, preferably about 5 µg to 1000 µg for a 70 kg patient per dose. Immunizing doses followed by boosting doses at established intervals, e.g., from one to four weeks, may be required, possibly for a prolonged period of time to effectively immunize an individual. In the case of chronic infection, administration should continue until at least clinical symptoms or laboratory tests indicate that the viral infection has been eliminated or substantially abated and for a period thereafter.

The compositions and methods of the invention may include the administration of one or more co-adjuvants. Suitable co-adjuvants include, but—are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (PCT Publication No. WO 90/14837), containing 5% Squalene, 0.5% Tween 80, and 0.5% Span 85 formulated into submicron particles, (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see PCT Publication No. WO 99/30739, published Jun. 24, 1999); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S 109 (where serine is substituted for the wild-type amino acid at position 109), adjuvants derived from the CpG family of molecules, CpG dinucleotides and synthetic oligonucleotides which comprise CpG motifs (see, e.g., Krieg et al., Nature, 374:546 (1995) and Davis et al., J. Immunol., 160:870-876 (1998)) and PT-K9/G129 (where lysine is substituted for the wild-type-amino acid at position 9 and glycine substituted at position 129) (see, e.g., PCT Publication Nos. WO93/13202 and WO92/19265); (7) other substances that act as immunostimulating agents to enhance the effectiveness of the composition. See, e.g., U.S. Pat. No. 6,534,064; and (8) other ligands for Toll-like receptors in addition to CpG and RIBI adjuvants, such as bacterial flagellin (an effective adjuvant for CD4+ T cells; see *IJ. Immunol.* 169: 3914-9 (October 2002).

The pharmaceutical compositions for therapeutic or prophylactic treatment are intended for mucosal (oral, nasal, rectal, vaginal, tracheal, etc.), parenteral, topical, or local administration (Note that mucosal administration is different from topical administration, as mucosal administration refers to application of the vaccine to a mucosal surface such as a surface of the respiratory tract, gastrointestinal tract, reproductive tract, etc.). Typically, the pharmaceutical compositions are administered parenterally, e.g., intravenously, subcutaneously, intradermally, or intramuscularly. Topical administration may be to an airway surface, such as by droplet administration to a nasal surface or by inhalation administration of aerosolized particles to a nasal surface or the surfaces of other airway passages; or to skin such as for the treatment of wounds or scarring as discussed below. Thus, the invention provides compositions for topical (mucosal or non-mucosal) or parenteral administration which comprise a solution of the peptides or conjugates dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc.

Oral or mucosal delivery may be carried out in the manner described in U.S. Pat. No. 6,270,758 to Staats et al.

Where the antigen or immunogen is a protein or a peptide it may be delivered per se or by delivering a nucleic acid intermediate that causes the synthesis of the antigen or immunogen in the subject, such as described in U.S. Pat. No. 5,589,466 to Felgner et al.

The present invention may also be administered via liposomes, which serve to target the conjugates to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the composition to be delivered is incorporated as part of a liposome, alone or in conjunction with a molecule which binds to, for example, a receptor prevalent among lymphoid cells. These molecules would include monoclonal antibodies which bind to the CD45 antigen, or with other therapeutic or immunogenic compositions. Thus, liposomes filled with a desired composition of the present invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of liposome size, acid lability and stability of the liposomes in the blood stream. A variety of methods are available for preparing liposomes, as described in, e.g., Szoka, et al., Ann. Rev. Biophys. Bioeng. 9:467 (1980), U.S. Pat. Nos. 4,235,871, 4,501,728, 4,837,028, and 5,019,369, incorporated herein by reference.

The concentration of compositions of the present invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

For targeting to the immune cells, a ligand to be incorporated into the liposome can include antibodies or fragments thereof specific for cell surface determinants of the desired immune system cells, or any other suitable targeting molecule (e.g., reovirus protein sigma 1, which has been used to target antigens to the M cells of the Peyer's patch and other inductive tissues of the mucosal immune system). A liposome suspension containing a composition of the present invention may be administered intravenously, locally, topically, etc. in a dose which varies according to, inter alia, the manner of administration, the composition being delivered, and the stage of the disease being treated.

For solid compositions, conventional nontoxic solid carriers may be used. These may include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more conjugates of the invention, and more preferably at a concentration of 25-75%. Absorption enhancers and bioadhesives can optionally be included in the liquid or solid compositiions, e.g., to increase the delivery of proteins/peptides via mucosal routes.

For aerosol administration (this term including both liquid and dry powder aerosols), the compositions of the present invention are preferably supplied in finely divided form along with a surfactant and propellant. Typical percentages of the composition are 0.01-20% by weight, preferably 1-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic-polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery.

In another aspect, the present invention is directed to vaccines which contain as an active ingredient an immunogenically effective amount of a composition of the present invention as described herein. Carriers are well known in the art, and include thyroglobulin, albumins such as bovine serum albumin, tetanus toxoid, polyamino acids such as poly(lysine: glutamic acid), hepatitis B virus core protein, hepatitis B virus recombinant vaccine and the like. The vaccines can also contain a physiologically tolerable (acceptable) diluent such as water, phosphate buffered saline, or saline. In addition to the preferred adjuvant described herein the composition may include an additional adjuvant, such as complete or incomplete Freund's adjuvant, aluminum phosphate, aluminum hydroxide, alum, cyotkines, TLR ligands, etc. Upon immunization with a composition as described herein, via injection, aerosol, nasal, oral, transdermal or other route, the immune system of the host responds by producing an enhanced immune response, humoral and/or cellular.

Vaccine compositions of the invention are administered to a patient susceptible to or otherwise at risk of disease, to elicit and/or enhance an immune response against an antigenic determinant. Such an amount is defined to be an "immunogenically effective dose," either for therapeutic or prophylactic use. In this use, the precise amounts again depend on the patient's state of health and weight, the mode of administration, the nature of the formulation, etc., but generally range from about 1.0 µg to about 5000 µg per 70 kilogram patient, more commonly from about 10 µg to about 500 µg per 70 kg of body weight.

In some instances it may be desirable to combine the compositions of the present invention with vaccines which induce neutralizing antibody responses to infections and cancers of interest.

The compositions of this invention may also be used to make monoclonal or polyclonal antibodies. Such antibodies may be useful as potential diagnostic or therapeutic agents.

4. Methods of Treating Microbial Infections.

The methods and compositions described above may be used in treating microbial infections. As noted above, the present invention provides methods of treating microbial infections (e.g., bacterial, viral, fungal and protozoal infections) in subjects in need thereof. Examples of microbial infections that may be treated by such methods include but are not limited to Category A and B pathogens as defined by the CDC Biological Diseases/agents list (e.g. Anthrax (*Bacillus anthracis*), Plague (*Yersinia pestis*), Smallpox (*Variola major*), Tualernia (*Francisella tularensis*) Viral hemorrhagic fevers (e.g. Ebola, Lassa); *Listeria monocytogenes*, yeast infections. Examples also include pathogens that typically cause community as well as hospital aquired infections (Gram negative enterobacteria, *Escherichia coli Staphylococcus aureus, Streptococcus pyogenes*, other gram positive bacteria most fungi and parasites). Examples also include newly emerging pathogens such as SARS, pathogens involved in post operative infections, and pathogens causing localized dermal infections. A particular example is *Salmonella typhimurim*.

Thus in some embodiments microbes that may be treated by the present invention include bacteria from the family Enterobacteriaceae. In more preferred embodiments bacteria of a genus selected from the group consisting of: *Escherichia, Proteus, Salmonella, Klebsaiella, Providencia, Enterobacter, Burkholderia, Pseudomonas, Acinetobacter, Aeromonas, Haemophilus, Yersinia, Neisseria*, and *Erwinia, Rhodopseudomonas*, or *Burkholderia* may be treated by the methods of the invention.

In yet other embodiments, the microbes to be treated are Gram-positive bacteria and are from a genus selected from the group consisting of: *Lactobacillus, Azorhizobium, Streptococcus, Pediococcus, Photobacterium, Bacillus, Enterococcus, Staphylococcus, Clostridium, Butyrivibrio, Sphingomonas, Rhodococcus*, or *Streptomyces* In yet other embodiments, the microbes to be treated are acid fast *bacilli*, e.g., from the genus *Mycobacterium*.

In still other embodiments, the microbes to be treated are, e.g., selected from a genus selected from the group consisting of: *Methanobacterium, Sulfolobus, Archaeoglobu, Rhodobacter*, or *Sinorhizobium*.

In other embodiments, the microbes to be treated are fungi, such as a fungus from the genus *Mucor* or *Candida*, e.g., *Mucor racemosus* or *Candida albicans*.

In other embodiments, the microbes to be treated are protozoa. In a preferred embodiment the microbe is a malaria or cryptosporidium parasite.

Routes of administration and pharmaceutical formulations for treating microbial infections include those described above in connection with vaccine adjuvant administration. Dosage of the mast cell membrane activator to the subject for treating microbial infections may range from about 0.05, 0.1, 0.5 or 1 milligram per kilogram subject body weight, up to about 10, 50 or 100 milligrams per kilogram subject body weight, or more.

The mast cell activators may be administered in combination or concurrently with other antimicrobial drugs, including but not limited to those described in U.S. Pat. No. 6,346,391 to Oethinger et al.

5. Wound Treatment.

The methods and compositions described above may be used in wound treatments. As noted above, the present invention provides a method of enhancing wound healing in a subject in need thereof, comprising administering (e.g., by topical administration to a wound or wound tissue) a mast cell membrane activator such as Compound 48/80 to a subject afflicted with a wound in an amount effective to enhance healing of the wound. In addition, the present invention provides a method of reducing scar formation in a subject in need thereof, comprising administering (e.g., by topical administration to a wound or wound tissue) a mast cell membrane activator such as Compound 48/80 to a subject afflicted with a wound in an amount effective to reduce scar formation during healing of said wound. Any type of surgical or traumatic wound may be treated, including wounds to the skin or skin tissue, as well as internal tissues such as muscle and connective tissues. Wound types that may be treated include wounds that are incisions, lacerations, burns, punctures, crushes, etc. Any increase in the speed or rate of wound healing is considered of benefit, and any decrease in scar tissue of clinical or cosmetic benefit is considered of benefit in the present invention. For treating wounds the route of administration may be a topical application to the wound or wound tissue as noted above, with a topical formulation such as described above. The topical formulation may include the mast cell membrane activator in any suitable amount, such as from 1 or 2 micrograms per milliliter up to 100, 200, 500 or 1000 micrograms per milliliter, or more. The topical formulation may optionally include a permeability enhancer in any suitable amount (e.g., one to 50, 90 or 99 percent by weight), with examples of permeability enhances including but not limited to diols such as propylene glycol and glycerol; monoalcohols such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones (azones); any of the permeation enhancers described in, for example, U.S. Pat. No. 5,445,611, etc.

The present invention is explained in greater detail in the following non-limiting Examples.

Example 1

While palpable swelling of regional lymph nodes is a common sequela of microbial infections, the mechanism responsible for this is poorly understood. Here we show that upon activation, peripheral mast cells secrete TNF-α, and that this mast cell product rapidly accumulates in draining lymph nodes and functions to initiate nodal hypertrophy. Following intradermal injection of bacteria, draining lymph nodes of wild type, but not mast cell deficient mice, undergo significant swelling. Instillation of the mast-cell-specific activator, compound 48/80, induces significant lymph node hypertrophy and specifically increases the recruitment of circulating T cells and the nodal expression of vascular cell adhesion molecule −1 (VCAM-1).

I. Methods

Mice and reconstitution with in vitro derived bone marrow mast cells. Both male mast cell deficient (WBB6F1-W/Wv) indicated in the text as W/Wv and congenic littermate control mice (WBB6F1-+/+) indicated in the text as +/+, as well as male TNF-α deficient (B6; 129S6-Tnf tm1Gkl) and age matched control mice (B6129SF2/J) were purchased from Jackson Laboratories (Bar Harbor, Me.) at 6-7 weeks of age. These strains were housed under pathogen free conditions in the Duke University vivarium until experiments were performed. Mast cell deficient mice were repleted with in vitro derived bone marrow mast cells from congenic controls. Bone marrow from femurs was flushed out and grown in RPMI medium containing 10% FBS, penicillin/streptomycin, HEPES, trypsin inhibitor, sodium pyruvate, rIL-3 (5 ng/ml) and stem cell factor (5 ng/ml) for a period of 4 weeks at which time the resulting cell cultures were determined to be >97% mast cells by toluidine blue staining. $5 \times 10^6$ cells were injected into the footpads of mast cell deficient mice and allowed to mature for 3 weeks. These mice were then used in experiments as repleted mast cell deficient mice. Male C57BL/6 (7-8 weeks old) mice were purchased from the NCI animal production facility and were housed in the Duke University animal facility under standard conditions. All mice were used between 8-12 weeks of age.

Infection and instillation of compound 48/80 and TNF-α antibody blocking. For infections, *E. Coli* J96 strain was heat killed at 62 C for 30 minutes. No viable colonies grew on McConkey agar and bacteria were determined to be undegraded by microscopy. $1 \times 10^7$ bacteria (as determined by optical density) was injected into the footpads of mice in a volume of 50 μl normal saline as a vehicle. Draining popliteal lymph nodes were removed at 24 hours post-infection and weights determined. Lymph nodes were frozen in OCT compound and sections were cut on a cryostat (Leica) 50 nm apart, fixed and stained with H&E. In a separate experiment, footpads were removed from mice at 1, 2, and 4 hours post infection, frozen in OCT compound sections were cut 50 nm apart, fixed with Carnoy's fixative, and stained with toluidine blue. Compound 48/80 (Sigma) was injected into footpads at 1.2 mg/kg mouse weight (C57BL/6) and 0.6 mg/kg (TNF-α deficient mice) in normal saline as a vehicle in a volume of 20 μl/footpad. Control footpads were injected with normal saline alone. Draining popliteal lymph nodes were removed and weighed at various time points following injection. To assess blocking with TNF-α specific antibody 250 μg of rat anti mouse specific antibody or an isotype control antibody (Pharmingen) were injected in the peritoneums of mice 24 hours prior to treatment of footpads with 48/80. 50 ng of recombinant mouse TNF-α (R&D Systems) was injected into the footpads of normal mice and draining popliteal lymph nodes were removed and weighed 24 and 48 hours later. Normal saline was injected as a control.

Cytokine ELISA, RT-PCR, PCR, and western blotting. Extracted popliteal lymph nodes were put into 100 μl PBS on ice, freeze-thawed 5 times and homogenized. Solid material was pelleted and the supernatant was used to assay for the presence of TNF-α in an ELISA according to the manufacturer's instructions (R&D Systems). RNA was extracted from lymph node tissues by homogenization in 100 μl of TRIZOL (GIBCO). Volume was increased to 1 ml and extraction was performed according to the manufacturer's instructions. Extracted RNA was used for reverse transcription for one cycle 42° C. for 40 minutes, 99° C. for 5 minutes and 5° C. for 5 minutes. The RT-PCR product was used subsequently for PCR amplification (35 cycles) using an inflammatory cytokine kit from Maxim Biotech according to the manufacturer's instructions and products were separated in 2% agarose and visualized with an Eagle Eye II (Stratagene). For assessment of VCAM-1 protein levels, lymph nodes from 48/80 treated mice were placed into 50 μl buffer, freeze-thawed once, and homogenized. Whole lymph node homogenates were assessed for protein content and run on a denaturing polyacrylamide (10%) gel. 20 μg of each preparation was loaded onto the gel. Proteins were transferred overnight to a PVDF membrane and the membrane was probed with a goat anti-mouse VCAM-1 monoclonal antibody (R&D Systems) at 1:1000 followed by a donkey anti-goat-HRP secondary antibody (Santa Cruz Biotechnology). Proteins were visualized by chemiluminescence substrate and exposed to film. Actin was run as a protein loading control.

T-cell trafficking A single cell suspension was obtained from spleens of 10-12 week old C57BL/6 mice using a 70 μm cell strainer into HBSS+5% FBS. Negative selection for total CD4 T-cells was performed using the following biotinylated antibodies: anti-CD8, B220, IgM, I-A/1-E, F4/80, CD11b, CD11c, Gr-1, and TER119. RBC were lysed and the remaining cell suspension was incubated with streptavidin-magnetic beads. The entire preparation was applied to a MACS column (Miltenyi Biotec) and the flow through cells were collected. This T-cell population was washed with PBS and labeled with CFSE (1 μM) per the manufacturer's (Molecular Probes) instructions. $5 \times 106$ labeled T-cells were introduced intravenously into C57BL/6 mice followed immediately by injection of compound 48/80 into the footpads. To assess specific T-cell activation isolated T-cells were treated prior to labeling with 100 ng/ml pertussis toxin (List Biological Labs) for two hours at 37 C washed twice and injected intravenously as described. Draining popliteal lymph nodes were excised, pooled, and a single cell suspension prepared in PBS. Cells were counted and fixed with 0.4% paraformaldehyde and the percentage of labeled T-cells in the lymph nodes was assessed by FACS.

II. Results

To study the mechanism of infection-initiated nodal hypertrophy, we employed a mouse model of localized infection, whereby bacteria were injected into the footpads of mice and at various time periods thereafter, the growth of the draining (popliteal) nodes was monitored. The bacterium employed was a well described pathogenic strain of *E. coli* (D. M. Baorto et al., Nature 389, 636-9 (Oct. 9, 1997)). Following instillation of $1 \times 10^7$ heat-killed bacteria into the footpads, lymph node hypertrophy was discernable as early as 6 hrs with the most marked and significant increase observed at 24 hr (FIG. 1a). The magnitude of nodal size increase is illustrated in cross sections of popliteal nodes obtained at 0 hr and 24 hr following infection (FIG. 1b). The figure also reveals that the increase in nodal weight was reflective of an increase in cellularity rather than fluid accumulation. Microscopic determination of cell populations in the nodes also confirmed this point (data not shown). It is also noteworthy that lymph node hypertrophy was observed in the local, popliteal, nodes and not in more distal nodes (data not shown).

Reasoning that the source of the "signal" for lymph node remodeling must be the site of bacterial injection, we examined this site more closely (P. Matzinger, Science 296, 301-5 (Apr. 12, 2002)). Thin frozen sections of footpads, injected with either bacteria or vehicle, were prepared at various time points and stained with the granule-specific stain, Toluidine Blue. A striking finding was that within minutes of bacterial instillation, local mast cells appeared degranulated and by 4 hrs, over 70% had totally degranulated and were no longer detectable by the granule-specific stains (FIG. 1c). The extent of mast cell degranulation between bacteria and control injected mice is illustrated in FIG. 1d. Thus, peripheral mast cells are early responders to infection and their responses involve the rapid degranulation and release of inflammatory mediators. To better define the specific contribution of mast cells, we compared bacteria-induced popliteal node hypertrophy in wild type (+/+) and mast cell deficient (W/Wv) mice at the 24 hr time point. A dramatic and significant difference was observed in lymph node hypertrophy between +/+ and W/Wv mice (FIG. 1e). To confirm the specific role of mast cells in lymph node hypertrophy, we repleted the footpads of W/Wv mice with bone marrow mast cells as described in the methods section and then challenged them with bacteria as before. Lymph node hypertrophy in mast cell-repleted W/Wv mice, was comparable to that of +/+mice and significantly higher than that observed in W/Wv mice (FIG. 1e).

Hence, mast cells were specifically involved in bacteria triggered lymph node hypertrophy. Was this outcome unique to bacteria or could a mast cell-specific secretagogue also achieve this effect? We examined the effect of compound 48/80, a reagent capable of exclusively activating mast cells in vivo (B. L. Diaz et al., *Int Arch Allergy Immunol* 111, 36-43 (September, 1996); M. Aridor et al. *J Cell Biol* 111, 909-17 (September, 1990); S. J. Getting et al., *J Pharmacol Exp Ther* 283, 123-30 (October, 1997); P. McLean et al., *J Exp Med* 192, 367-80 (Aug. 7, 2000)). Compound 48/80 was instilled into the footpads of wild type mice and at different time points, popliteal nodes were examined for hypertrophy. As in the case of bacteria, a relatively rapid growth in lymph node size was observed (FIG. 1f). Taken together these data demonstrate that peripheral mast cells are specifically involved in modulating hypertrophy of draining lymph nodes, presumably through the release of one or more of its mediators. Because of its intrinsic capacity to activate mast cells, compound 48/80 is a valuable tool for achieving specific activation of mast cells in vivo and thus, was used for all subsequent studies.

Figure 2:
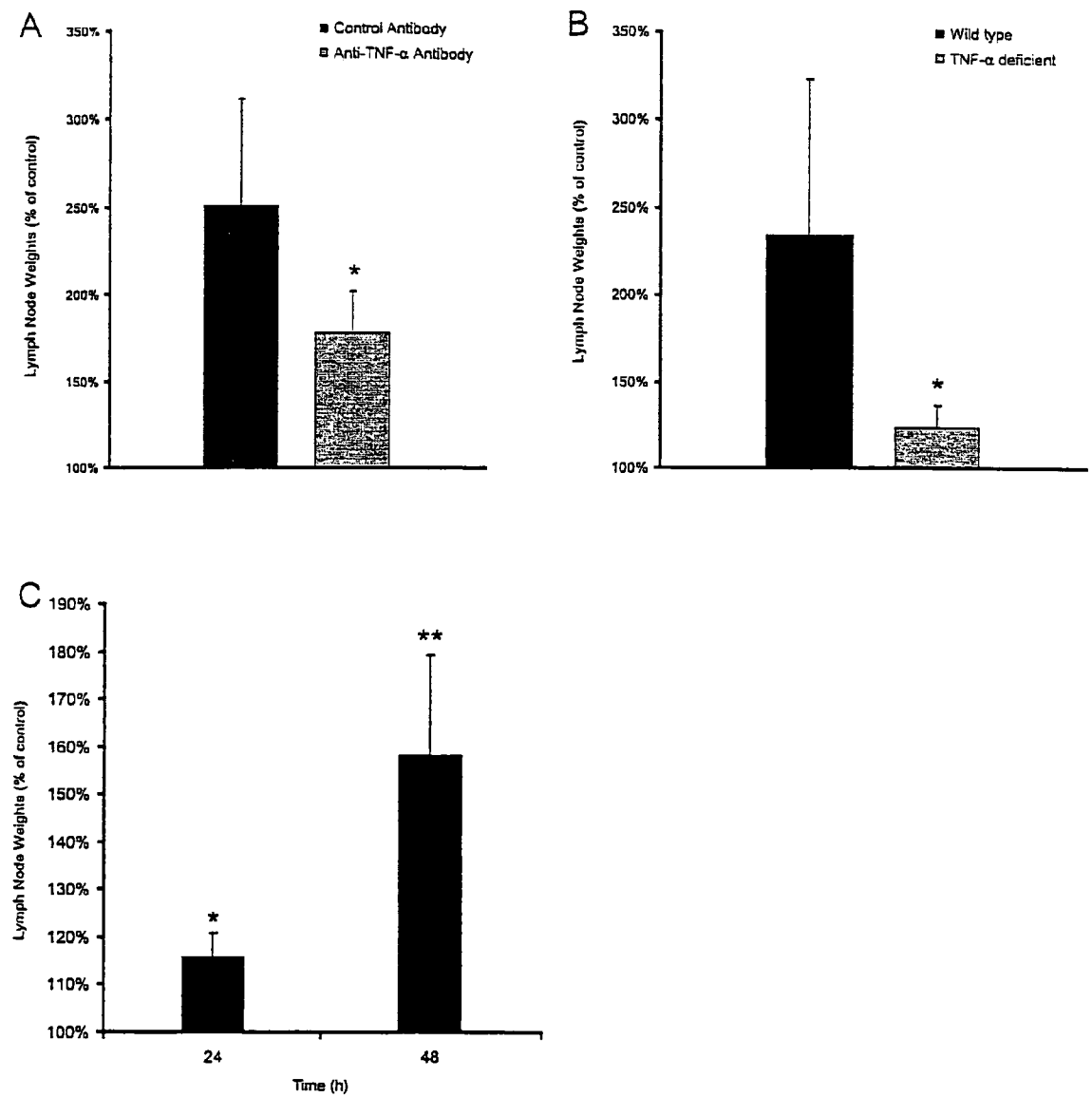
FIG. 2 Regulation of lymph node hypertrophy by mast cell derived TNF-α.

A mast cell cytokine singularly capable of mediating lymph node hypertrophy is TNF-α. This cytokine promotes entrapment and extravasation of lymphocytes from the vasculature (Z. Ding et al. *J Leukoc Biol* 67, 825-33 (June, 2000); Z. Ding et al., *J Leukoc Biol* 69, 458-66 (March, 2001); P. Estess et al., *J Exp Med* 190, 9-19 (Jul. 5, 1999); T. Carlos et al., *Blood* 84, 2068-101 (Oct. 1, 1994)). Because mast cells are the only cell type capable of storing preformed TNF-α they provide an immediate source of TNF-α in peripheral tissue during infection (J. Gordon and S. Galli, *J Exp Med* 174, 103-7 (Jul. 1, 1991); J. Gordon and S. Galli, *Nature* 346, 274-6 (Jul. 19, 1990)). We investigated if mast cell-derived TNF-α was draining to the regional nodes- and mediating their hypertrophy. To establish that the mediator responsible for lymph node hypertrophy was mast cell-derived TNF-α, we examined the in vivo effect of blocking the activity of TNF-α specifically evoked from mast cells. We examined the effect of TNF-α specific neutralizing antibodies on the nodes of 48/80 injected mice. Compared to control mice, immunized with antibodies to an irrelevant antigen, mice immunized with TNF-α-specific antibody exhibited significantly less lymph node hypertrophy (FIG. 2a). Additionally we employed TNF-α deficient mice and compared lymph node weights following footpad instillation of compound 48/80. The nodal growth observed in TNF-α deficient mice was significantly reduced compared to wild type mice (FIG. 2b). Thus, mast cell derived TNF-α was necessary for lymph node hypertrophy but was it sufficient? Conceivably, other mast cell products, in concert with TNF-α, were responsible for this effect. We examined the effect of directly injecting TNF-α into the footpads of mice. A marked lymph node hypertrophy was observed but interestingly, the kinetics of this response was different, with maximal lymph node growth observed at 48 and not by 24 hrs (FIG. 2c). Although TNF-α was sufficient for lymph node hypertrophy, other mast cell products appear to contribute, perhaps by accelerating nodal hypertrophy.

Based on the rapid changes observed in draining nodes, we investigated TNF-α levels in these structures at various time points following activation of peripheral mast cells. Nodal homogenates of mice injected with compound 48/80 were prepared at different time points and then assayed for TNF-α by ELISA. As shown in FIG. 3a, a distinct spike in TNF-α levels was detected at 3 hr. An examination of nodal tissue homogenates for mRNA to an array of proinflammatory mediators including TNF-α revealed that with the exception of constitutive production of TGF-β, no messages for TNF-α or other mediators was detected in the nodes during the first 3 hrs after activation by compound 48/80 (FIG. 3b). Hence, the spike of nodal TNF-α was not locally derived, suggesting that 3 hours represents the time it took for peripheral TNF-α to reach the node following mast cell degranulation.

Finally, we investigated the hypertrophic node generated by compound 48/80 to elucidate the mechanism of lymph node remodeling. We fluorescently labeled spleen derived total CD4 T cells and intravenously introduced them into mice. Footpads of these mice were injected with 48/80 or vehicle (controls) and after 24 hours, T cell sequestration in each of the nodes was determined by FACS. A 3-fold greater nodal entrapment of T cells occurred in 48/80 treated mice compared to controls, indicating that compound 48/80 induced sequestration of T cells (FIG. 4a) To determine specificity of T-cell sequestration in lymph nodes we pretreated T-cells with pertussis toxin and intravenously injected these cells into mice whose footpads had been injected with 48/80. This treatment inhibited T-cell recruitment to draining lymph nodes indicating that specific T-cell activation is required during this response (FIG. 4a) (J. Cyster and C. Goodnow, *J Exp Med* 182, 581-6 (Aug. 1, 1995); R. Bargatze and E. Butcher, *J Exp Med* 178, 367-72 (Jul. 1, 1993); R. Warnock et al. *J Exp Med* 187, 205-16 (Jan. 19, 1998)). Since sequestration of lymphocytes in nodes has been attributed, at least in part, to the upregulation of VCAM-1 in endothelial cells (C. Berlin-Rufenach et al., *J Exp Med* 189, 1467-78 (May 3, 1999); C. Faveeuw et al., *Int Immunol* 12, 241-51 (March, 2000)), we examined if this adhesion molecule was upregulated in draining nodes following 48/80 challenge. As shown in FIG. 4b, there appeared to be at least a 3-fold upregulation in the amounts of VCAM-1 expressed in nodal homogenates in 48/80 treated mice compared to vehicle treated controls. Thus the 48/80 induced nodal hypertrophy is the result of T cell sequestration in the nodes which occurs in parallel with the upregulation of VCAM-1.

For effective defense against infections, continual preparation and anticipation on the part of the host is required. Upon recognizing molecular markers of infection, the host swiftly triggers the innate as well as the adaptive immune systems. Here we show that through the continual production and storage of proinflammatory mediators, mast cells lie poised beneath the dermis ready to secrete their contents and instantly alert the host to infection. In addition to initiating the innate immune responses locally (R. Malaviya et al., Abraham, *Nature* 381, 77-80 (May 2, 1996); B. Echtenacher et al., *Nature* 381, 75-7 (May 2, 1996)), the rapidly released mediators of mast cells drain to regional lymph nodes and orchestrate the intricate initiation of the adaptive immune system.

Only by maintaining prestored caches of proinflammatory mediators within mast cells, is the host able to readily sense microbial attack at peripheral sites. Within hours of peripheral mast cell activation, presynthesized TNF-α accumulates in the draining nodes and triggers the recruitment of circulating T cells. Although TNF-α has been implicated in the early host response to infection (T. van der Poll and S. van Deventer, *Infect Dis Clin North Am* 13, 413-26, ix (June, 1999)), its involvement in lymph node hypertrophy represents a mechanism by which mast cells regulate lymph node architecture and initiate the adaptive immune response.

It has previously been demonstrated that peripheral tissues produce various effector molecules capable of draining to regional nodes, and in so doing, regulate these structures via remote control (R. Palframan et al., *J Exp Med* 194, 1361-73 (Nov. 5, 2001)). By storing presynthesized mediators including TNF-α, mast cells are a primary source of such effector molecules in peripheral tissue. In vivo, presynthesized mast cell products would be expected to reach draining nodes long before products from other cells synthesized de novo in response to infection. Though traditionally viewed as a mediator of allergy, anaphylaxis and immune dysfunction, these findings reveal a critical role for mast cells in initiating the most advanced mechanisms of host defense.

Example 2

Dose-Response Adjuvant Study

FIG. 5 shows antigen-specific antibody serum (IgG) and mucosal (IgA) responses using compound 48/80 as an nasal vaccine adjuvant.

FIG. 5A, (C57BL/6×BALB/c)F1 female mice were nasally immunized with recombinant *Bacillus anthracis* protective antigen (rPA) alone or in the presence of cholera toxin (CT) or four-fold serial dilutions of compound 48/80 (48/80). Immunizations were instituted on days 0, 7, and 14. On day 21-22 (FIG. 5A), serum was collected and tested for the presence of anti-PA IgG. Both CT and 48/80 provided significant adjuvant activity at all doses tested as indicated by the anti-PA IgG geometric mean titers indicated ($p<0.05$). Compound 48/80 used at 125, 31 and 8 μg was as effective as CT when used as a nasal vaccine adjuvant based on antigen-specific IgG serum titers ($p<0.05$)

FIG. 5B-D shows antigen-specific vaginal, salivary and fecal IgA responses in (C57BL/6×BALB/c)F1 female mice nasally immunized with recombinant *Bacillus anthracis* protective antigen (rPA) alone or in the presence of cholera toxin (CT) or two-fold serial dilutions of compound 48/80 (48/80). Immunizations were instituted on days 0, 7, and 14. On day 28 vaginal lavage, saliva and feces was collected and tested for the presence of anti-PA IgA. 48/80 provided significant adjuvant activity for the induction of vaginal and fecal antigen-specific IgA when used at 125 and 31 μg (FIGS. 5B and 5C respectively; $p<0.05$). 48/80 provided significant adjuvant activity for the induction of salivary antigen-specific IgA when used at 125, 31, and 8 μg (FIG. 5D; $p<0.05$).

Example 3

Adjuvant Activity

Female (C57BL/6×BALB/c)F1 mice were nasally immunized with 10 μg recombinant protective antigen (rPA) alone or in the presence of 1 μg cholera toxin (CT) or 8 μg compound 48/80 (48/80) on days 0, 7, and 140 n day 175, serum was collected and tested for the presence of anti-PA IgG by ELISA. As shown in FIG. 6, both CT and 48/80 showed a significant adjuvant activity over PA alone ($p=0.001$ and 0.002 respectively). This demonstrates the long lasting nature of 48/80 as an effective adjuvant.

Example 4

Induction of Protective Antibody Responses

Female (C57BL/6×BALB/c)F1 mice were nasally immunized with recombinant *Bacillus anthracis* protective antigen (rPA) alone or in the presence of cholera toxin (CT) or in the presence of 125 μg compound 48/80 (48/80). Day 22 serum was tested for the presence of antibodies that could neutralize the toxicity of anthrax lethal toxin using a macrophage anthrax toxin toxicity assay. In this assay, lethal toxin kills macrophages (low optical density) and in the presense of protective anti-PA antibodies, the macrophages survive (high optical density). Sera (diluted 1:8) from naïve mice, mice immunized with PA alone, or mice immunized with PA plus CT failed to prevent lethal toxin induced death in macrophages (FIG. 7). In contrast, serum from mice immunized with PA plus 48/80 provided complete protection from antrax lethal toxin induced cell death (FIG. 7) These results suggest that while antigen specific IgG antibody endpoint titers are comparable when using CT or 48/80 as an adjuvant (FIG. 5A), the neutralization activity of the sera collected from animals immunized with PA plus 48/80 was qualitatively better (i.e. toxin neutralization activity) than sera collected from animals immunized with PA plus CT.

Example 5

Adjuvant Activity with Diphtheria Toxoid in Various Mouse Strains

Swiss Webster, C57B1/6, and BALB/c mice were nasally immunized with diphtheria toxoid (DT) plus or minus 48/80 to confirm the adjuvant activity of 48/80 when administered with a different antigen in various mouse strains. Mice were nasally immunized with 15 μg DT alone, with CT (1 μg, positive control) or 31 μg of −48/80. FIG. 8 shows that anti DT serum IgG responses in mice nasally immunized with 48/80 were significantly-greater than anti DT serum IgG responses in mice nasally immunized with DT alone in all three mouse strains. These results indicate that 48/80 is an effective adjuvant in Swiss Webster, C57B1/6, and BALB/c mice.

Example 6

Treatment of Microbial Infections

FIG. 9 shows that co-injection of Compound 48/80 with *Salmonella typhimurim* into the peritoneal cavities of mice markedly reduces bacterial growth. As shown in the figure, mice have limited capability to control the in vivo growth of *Salmonella*. Notice the marked effect of compound 48/80 in reducing bacterial growth.

FIG. 10 shows that the addition of Compound 48/80 at the site of bacterial instillation (peritoneum) markedly reduces the ability of *Salmonella* to migrate into and colonize other body sites. This figures shows the effect of compound 48/80 on the systemic spread of *Salmonella* to other, more distal, sites.

FIG. 11 shows that the addition of compound 48/80 at sites of infection (peritoneal cavity) markedly increases local production of several neutrophil chemoattractants. Each of these chemoattractants is typically produced by activated mast cells.

FIG. 12 shows that instillation of compound 48/80 into the peritoneal cavities of mice results in increased recruitment of neutrophils compared to controls instilled only with *Salmonella*. The increased levels of neutrophils in 48/80 treated mice correlates with increased presence of mast cell chemoattractants. This data also correlates with increased bacterial clearance in 48/80 treated mice. Note that neutrophils represent the major cell type responsible for clearance of *Salmonella*.

Figure 13:
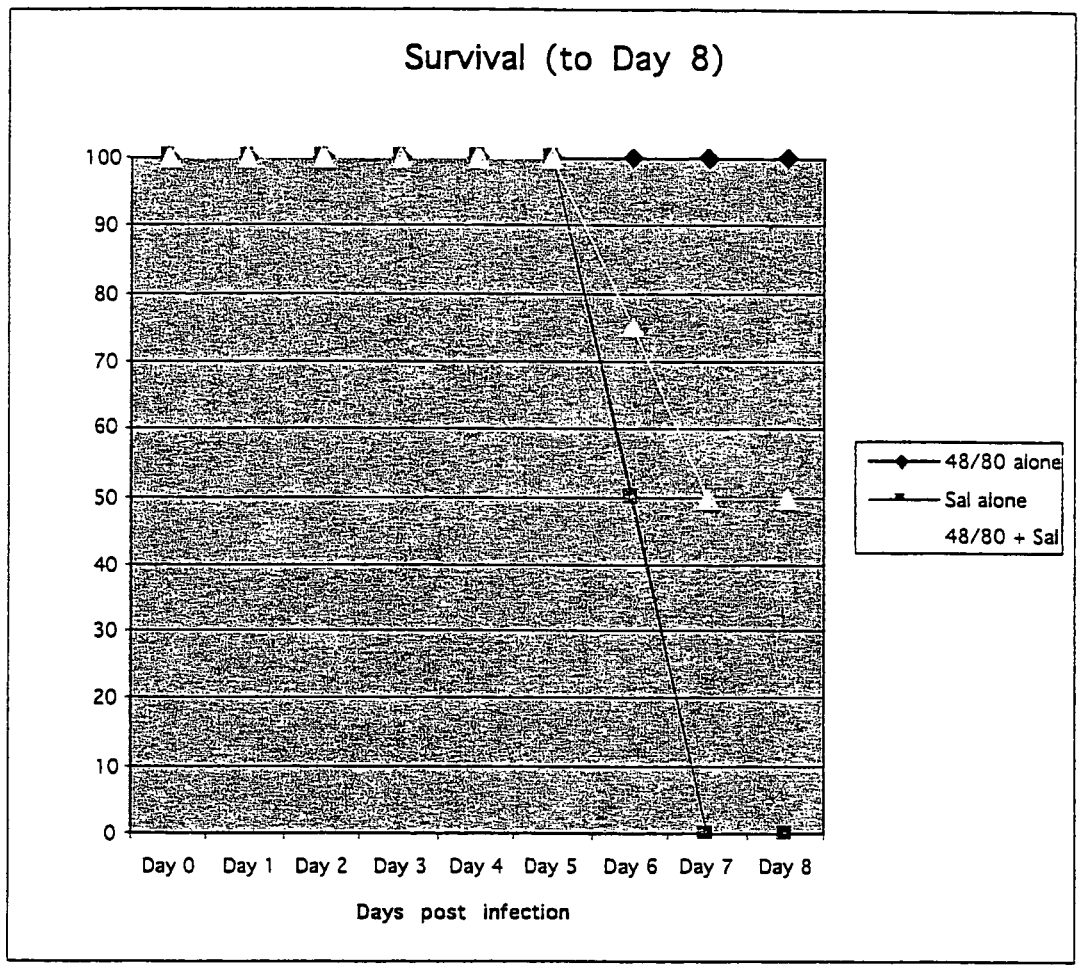
FIG. 13 shows the protective effect of compound 48/80 when given orally to Salmonella infected mice.

FIG. 13 shows the protective effect of compound 48/80 when given orally to *Salmonella* infected mice. The agent was given 2 hours after a lethal dose of *Salmonella* was orally instilled.

The foregoing is illustrative of the present invention, and is not to be construed as limiting thereof. The invention is defined by the following claims, with equivalents of the claims to be included therein.

That which is claimed is:

1. A method of inducing an immune response comprising concurrently administering an immunogen and compound 48/80 to a subject in an amount effective to produce an immune response therein, wherein said compound 48/80 is administered in an adjuvant-effective amount and wherein said immunogen and said compound 48/80 are administered simultaneously in a common pharmaceutical carrier.

2. The method of claim 1, wherein said administering step is carried out by parenteral administration.

3. The method of claim 1, wherein said immune response is a prophylactic immune response.

4. The method of claim 1, wherein said immune response is a therapeutic immune response.

5. The method of claim 1, wherein said immune response comprises a humoral immune response.

6. The method of claim 1, wherein said immune response comprises a cellular immune response.

7. The method of claim 1, wherein said administering step is carried out by mucosal administration.

8. A method of enhancing a protective immune response to an immunogen, comprising concurrently administering the immunogen and compound 48/80 to a subject in an amount effective to enhance a protective immune response relative to an immune response produced by administering the immunogen in the absence of compound 48/80, wherein said compound 48/80 is administered in an adjuvant-effective amount and wherein said immunogen and said compound 48/80 are administered simultaneously in a common pharmaceutical carrier.

9. The method of claim 8, wherein said administering step is carried out by parenteral administration.

10. The method of claim 8, wherein said administering step is carried out by mucosal administration.

11. The method of claim 8, wherein said protective immune response is a prophylactic immune response.

12. The method of claim 8, wherein said protective immune response is a therapeutic immune response.

13. The method of claim 8, wherein said protective immune response comprises a humoral immune response.

14. The method of claim 8, wherein said protective immune response comprises a cellular immune response.

15. A method of providing adjuvant activity to an immunogen, comprising concurrently administering the immunogen and compound 48/80 to a subject in an amount effective to produce a protective immune response, wherein said compound 48/80 is administered in an adjuvant-effective amount and wherein said immunogen and said compound 48/80 are administered simultaneously in a common pharmaceutical carrier.

16. The method of claim 1, wherein the subject is a human.

17. The method of claim 8, wherein the subject is a human.

18. The method of claim 15, wherein the subject is a human.

* * * * *

UNITED STATES PATENT AND TRADEMARK OFFICE
CERTIFICATE OF CORRECTION

| | | |
|---|---|---|
| PATENT NO. | : 8,076,059 B2 | Page 1 of 1 |
| APPLICATION NO. | : 10/817023 | |
| DATED | : December 13, 2011 | |
| INVENTOR(S) | : Pizzo et al. | |

It is certified that error appears in the above-identified patent and that said Letters Patent is hereby corrected as shown below:

<u>In the Patent</u>:

Column 19, Line 66: Please correct "and 140 nday" to read -- and 14. On day --

Column 20, Line 43: Please correct "–48/80" to read -- 48/80 --

Signed and Sealed this
Tenth Day of April, 2012

David J. Kappos
*Director of the United States Patent and Trademark Office*